United States Patent [19]

Scott et al.

[11] 4,224,934

[45] Sep. 30, 1980

[54] MEDICAL PROSTHETIC PULL VALVE AND SYSTEM FOR USING SAME

[75] Inventors: F. Brantley Scott, Houston, Tex.; John H. Burton, Minneapolis, Minn.

[73] Assignee: American Medical Systems, Inc., St. Louis Park, Minn.

[21] Appl. No.: 28,979

[22] Filed: Apr. 11, 1979

[51] Int. Cl.³ ............................................. A61F 5/00
[52] U.S. Cl. .................................................... 128/79
[58] Field of Search ................. 128/79, DIG. 25, 274; 251/339–344, 347, 348; 137/DIG. 2

[56] References Cited

U.S. PATENT DOCUMENTS

| | | | |
|---|---|---|---|
| 1,880,948 | 10/1932 | Evennett | 251/342 |
| 2,623,787 | 12/1952 | Smith | 251/342 |
| 2,999,499 | 9/1961 | Willet | 251/342 |
| 3,530,928 | 9/1970 | Swinney | 251/342 |
| 3,570,484 | 3/1971 | Steer et al. | 128/274 |
| 3,685,795 | 8/1972 | Caster | 251/342 |
| 3,971,541 | 7/1976 | Griffin | 251/347 |
| 4,009,711 | 3/1977 | Uson | 128/79 |

Primary Examiner—Lawrence W. Trapp
Attorney, Agent, or Firm—Williamson, Bains, Moore & Hansen

[57] ABSTRACT

A prosthetic check valve which allows unrestricted fluid flow in a forward direction and is capable of being repeatedly pulled open to allow reverse fluid flow. The valve comprises a valve body having an extensible section which houses a valve seat and a valve support. A resilient member is attached to the valve support and resiliently supports a valve member so as to force the valve member towards the valve seat. When the extensible section is contracted, the valve acts as a check valve to allow fluid flow only in a forward direction from a supply tube, through the valve support and valve seat, to a demand tube. When the extensible section is extended, fluid is allowed to flow both in the aforesaid forward direction and in a reverse direction through the valve.

14 Claims, 7 Drawing Figures

U.S. Patent  Sep. 30, 1980  4,224,934
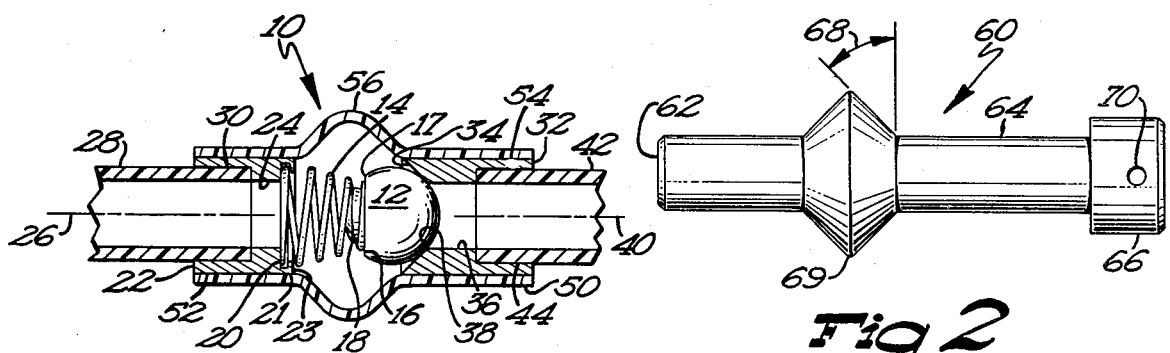
Fig 1  Fig 2
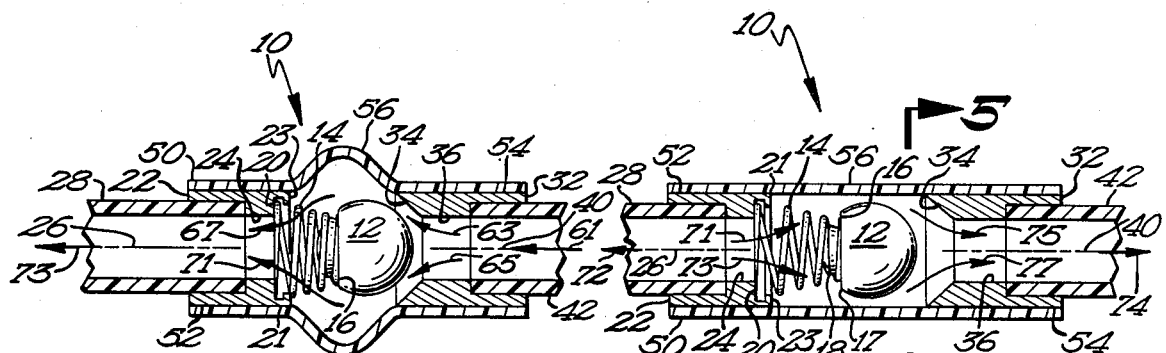
Fig 3  Fig 4
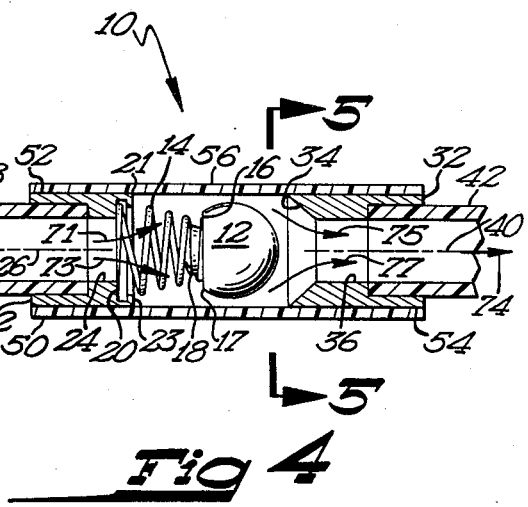
Fig 5
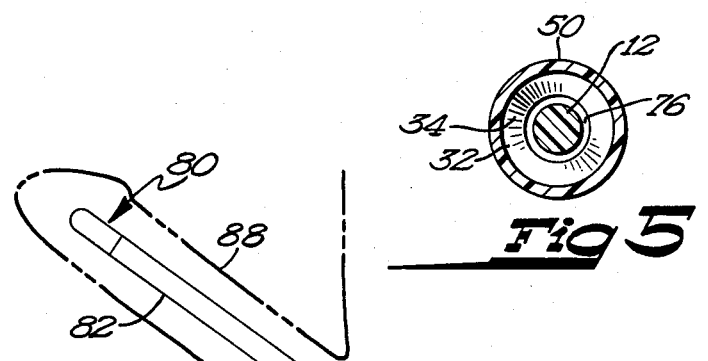
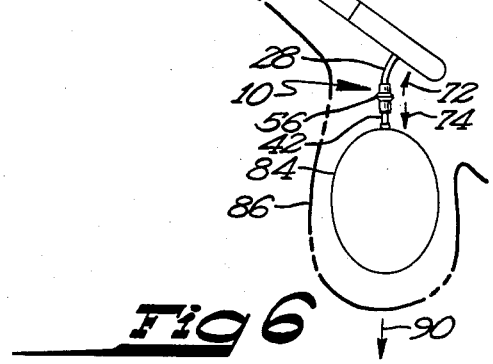
Fig 6
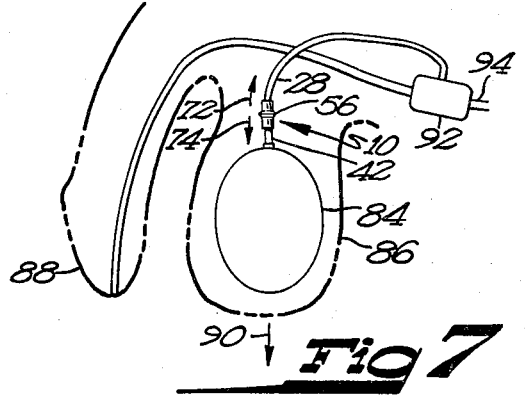
Fig 7

MEDICAL PROSTHETIC PULL VALVE AND SYSTEM FOR USING SAME

BACKGROUND OF THE INVENTION

This invention relates generally to medical prosthetic systems, and particularly to implantable devices which make use of a valve to control inflation of a prosthesis.

Specially adapted valves have been used in the construction and operation of various inflatable prosthetic devices designed for medical implantation. Such devices have been designed to aid in the treatment of urological disorders including erectile impotence, urinary incontinence, and fecal incontinence. A device usable to cure erectile impotence is described by Robert Buuck in U.S. Pat. No. 3,954,102. The patent discloses a check valve including a Teflon ball housed within a silicone rubber tube and a bypass valve making use of similar components. The bypass valve opens when deformed by being squeezed laterally. Another patent by the same inventor (U.S. Pat. No. 3,863,622) discloses an implantable device suited to controlling either the flow of urine or fecal waste. Check valves which make use of a helical coil spring are shown therein. A valve usable in controlling an inflatable penile prosthesis is disclosed by Aurelio Uson in U.S. Pat. No. 4,009,711. Uson shows a valve which acts as a check valve in one direction and may be squeezed gently to allow reverse fluid flow.

Prior art valves adapted for physiological drainage, such as Schulte, U.S. Pat. No. 3,758,073 have relied upon lateral compression forces to allow reverse flow. Such valves cannot be placed in remote locations since they must be accessible to the user. Also, such valves are difficult for the user to locate and hold in place. If a large amount of lateral compression or a large amount of squeezing is required for the operation of implantable valves, nearby living tissues which are subjected to high stresses during the compression or squeezing may become inflamed and damaged. Also, high stresses will be caused in the valve structure thus encouraging fatigue failure and foreshortening the useful life of the valve. In many of the prior art devices, the patient must be instructed not to press the release valve too forcefully as excessive pressure will temporarily close rather than open the valve.

SUMMARY OF THE INVENTION

Accordingly, an object of the present invention is to provide a valve for use in medical prosthetic devices which acts as a check valve in one forward flow direction and is capable of being repeatedly pulled open to allow reverse fluid flow.

A further object of the invention is to provide a valve of the foregoing character which when implanted and in use, will not lead to the inflammation or damage of nearby living tissues. More specifically, an aim of the invention is to allow operation of the valve by a pulling action such that nearby living tissues are not subjected to high stresses. Thus, a purpose of the valve is to allow reverse fluid flow without leading to the inflammation or damage of nearby living tissues.

Another object of the invention is to provide a valve which can be operated by pulling on a relatively large, remote object such as the fluid reservoir of an inflatable medical prosthesis, such that the prosthesis will be more easily operable and the risk of inflammation or damage to nearby living tissues will be minimized.

A further object of the invention is to provide a valve which will not stop fluid flow when opened too forcefully, and thus will not cause the medical prosthesis to malfunction.

Yet another object of the invention is to provide a valve which is operable when placed in remote locations, including locations which are inaccessible to direct manual manipulation. Therefore, greater flexibility is afforded by this invention in allowing valve implantation in a variety of locations within the body.

Another object of the invention is to provide a method for manufacturing a medical prosthetic pull valve which incorporates an extensible section in the outer member of said valve by means of a molding process. Said method of manufacture also preferably includes a molding or cutting step performed on a seating member to form a seating surface.

Still another object of the invention is to provide implantable medical prosthetic systems making use of the above described pull valve cooperatively connected to other hydraulic components.

Briefly, the invention involves the structure, manufacturing method, and use of a medical prosthetic pull valve usable with inflatable implanted devices. Valving action occurs where a valve member contacts a seating member having a seating channel. The valve opens when the valve member breaks contact with the seating member. The valve member is supported by a resilient member so that the valve will open when forces exerted on the valve member by fluid flowing along the seating channel cause the resilient member to compress. The valves is also openable by the application of outside forces to an extensible section of the valve body such that the seating member is pulled away from the valve member. The medical prosthetic pull valve may be connected between a fluid reservoir and distensible cylinders to form an inflatable penile prosthesis, wherein the valve acts as a check valve to allow fluid to be pumped from the reservoir to the distensible cylinders and the valve is openable to allow fluid flow back from the distensible cylinders to the reservoir. Similarly, the medical prosthetic pull valve may be connected between a fluid reservoir and an occlusion means to control the discharge of urine or fecal waste.

These and other objects and advantages of this invention will be readily understood as the following description is read in conjunction with the accompanying drawings, wherein like reference numerals have been utilized to designate like elements throughout the several views.

DESCRIPTION OF THE DRAWINGS

FIG. 1 is a side sectional view showing the medical prosthetic pull valve in its closed position;

FIG. 2 is a side view showing a mold usable in the manufacture of the medical prosthetic pull valve;

FIG. 3 is a partially cut away side view showing the medical prosthetic pull valve in an open position allowing forward fluid flow;

FIG. 4 is a side sectional view showing the valve in an open position allowing forward and reverse fluid flow;

FIG. 5 is a cross sectional view of the medical prosthetic pull valve, the view being taken in the direction of the line 5—5 of FIG. 4;

FIG. 6 is a schematic view showing the medical prosthetic pull valve adapted for use in an inflatable penile prosthesis; and FIG. 7 is a schematic view showing the medical prosthetic pull valve adapted for use in a system for the treatment of urinary incontinence.

DESCRIPTION OF THE PREFERRED EMBODIMENT

Referring first to FIG. 1, the valve has been denoted generally by the reference numeral 10. Valve member 12 is positioned inside the valve 10, is preferably of spherical shape, and preferably is composed of a chemically inert substance such as that sold under the trademark Teflon. Valve member 12 is attached to a resilient member 14, which preferably comprises a right frustoconical helix formed from stainless steel wire. As shown in the drawing, resilient member 14 may be attached to valve member 12 by means of a groove 16 and ridges 17 and 18. A helical shape for resilient member 14 is especially advantageous inasmuch as one turn of the helix may be placed inside groove 16 and may be wedged between said ridge 17 and ridge 18. Groove 16 and said ridges 17 and 18 may be conveniently formed by mounting valve member 12 in the chuck of a lathe and cutting a portion of valve member 12 away using a turning tool.

Resilient member 14 is attached to support surface 20 of valve support 22, attachment preferably being achieved by applying an adhesive substance between resilient member 14 and support surface 20. During assembly of valve 10, ridge 21, which projects from support surface 20, serves to locate resilient member 14 with respect to valve support 22. Ridge 21 further cooperates with flap 23 to secure resilient member 14 in place while valve 10 is in use. Valve support 22 has a channel 24 allowing fluid flow therethrough, and preferably has a cylindrical shape with a support axis 26. Other parts of the medical prosthetic device such as a urethral occluder 92 (FIG. 7) or distensible cylinders 82 (FIG. 6) may be hydraulically connected to valve support 22 by means of demand tubing 28, preferably composed of flexible, biologically compatible meterial. Demand tubing 28 may be adapted to slidably mount inside channel 24 and be fixed in place by means of adhesive applied upon mating surface 30.

Seating member 32 is provided with a seating surface 34 shaped to conform with valve member 12 when the valve 10 is in its closed state. Seating surface 34 may be formed by cutting seating member 32 with a sharp object such as a razor blade or may be formed by molding the proper shape at the time that seating member 32 is formed. In its preferred shape, seating member 32 is a hollow circular cylinder having a seating axis 40, and seating surface 34 is shaped like the side of a right frusto-cone. Seating member 32 is further formed to include a channel 36 which is preferably shaped as a circular cylindrical bore coaxial with seating member 32. The diameter of the bore forming channel 36 is chosen so as to cooperate with the shape of seating surface 34 in forming an area of contact 38 between seating member 32 and valve member 12. Seating member 32 is preferably composed of a material softer than valve member 12, rendering said seating member 32 capable of conformably deforming to the shape of valve member 12. Surface forces formed at said area of contact 38 as a result of the deformation of seating member 32 act to grip valve member 12 and hold it in place against seating surface 34.

Other parts of the medical prosthetic device such as a fluid reservoir (FIGS. 6 and 7) may be hydraulically connected to seating member 32 by means of supply tubing 42, preferbly composed of flexible, biologically compatible material. Supply tubing 42 may be adapted to slidably mount inside channel 36 and be fixed in place by means of adhesive applied upon mating surface 44.

An outer member 50 preferably comprises a hollow tubular sheath which surrounds and encases valve support 22 and seating member 32. Outer member 50 is fixed to valve support 22 by means of adhesive applied upon mating surface 52. Similarly, outer member 50 is fixed to seating member 32 by means of adhesive applied to mating surface 54. Outer member 50 includes an extensible section 56 which is located between valve support 22 and seating member 32. Extensible section 56 is preferably formed by creating a circumferential fold or bulge in outer member 50.

Referring now to FIG. 2, a mold 60 for outer member 50 is shown. Mold 60 has a lower end 62, a shank portion 64, and an upper end 66. Shank portion 64 is preferably cylindrical in shape and includes a circumferential ridge 69. Said circumferential ridge preferably has sides sloping at an angle 68 of approximately 30 degrees as indicated in FIG. 2. Upper end 66 is equipped with a support hole 70. In practice, an outer member 50 (as in FIG. 1) is formed by dipping lower end 62 and shank portion 64 of mold 60 into a container of heat curing rubber dispersed in a solvent. A string or wire (not shown) may be slipped through support hole 70 to support mold 60 during the dipping process. Once the elastomeric coating on mold 60 has fully cured, a knife may be used to trim away the elastomer covering lower end 62, and the elastomer covering shank 64 may be slidably removed in one piece from mold 60. An alternate method of forming outer member 50 may be practiced by injecting elastomer into a hollow mold cavity (not shown).

The drawing in FIG. 3 shows the operation of valve 10 as a check valve when extensible section 56 is in a contracted state. Valve member 12 is displaced from seating surface 34 and resilient member 14 is compressed as would be the condition in use if the fluid pressure inside channel 36 is greater than the fluid pressure inside support channel 24. When extensible section 56 is in its contracted state, valve 10 opens only when the fluid pressure inside channel 36 is greater than the fluid pressure inside support channel 24 combined with the closing pressure exerted by spring 14 and the gripping forces at seating surface 34. Thus, fluid will flow only from supply tube 42 to demand tube 28 when extensible section 56 is in its contracted state. The direction of fluid flow is indicated in FIG. 3 by arrows labeled 61, 63, 65, 67 and 69.

Referring now to FIG. 4, valve 10 is shown as it would appear when extensible section 56 is in its extended state, as would occur when valve 10 is pulled apart by opposite, outward forces acting along support axis 26 and seat axis 40. The direction of such opposed forces is indicated on the drawing by arrows labeled 72 and 74. Section 56 may be extended to the position shown in FIG. 4 by the application of pulling forces in opposite directions thereon. When pulled apart as shown, valve 10 offers little resistance to flow from demand tube 28 to supply tube 42. One possible direction of fluid flow is indicated in FIG. 4 by arrows labeled 71, 73, 75 and 77.

FIG. 5 depicts a cross sectional view of valve 10 taken along the line 5—5 of FIG. 4. The drawing shows valve 10 in its open state such that fluid is allowed to pass through gap 76 defined by the space between valve member 12 and seating surface 34 of seating member 32. Outer member 50 is shown as surrounding seating member 32.

As shown in FIG. 6 of the drawings, the medical prosthetic pull valve 10 may be used as part of an inflatable penile prosthesis designated generally by the number 80. Inflatable penile prosthesis 80 includes one or more distensible cylinders 82 and a fluid reservoir 84. Said one or more distensible cylinders 82 are connected to valve 10 by means of demand tubing 28. Fluid reservoir 84 preferably takes the form of a squeezable bulb and is connected to valve 10 by means of supply tubing 42. The construction and operation of such a prosthesis to aid in the treatment of erectile impotence is fully described by Robert Buuck in U.S. Pat. No. 3,954,102. For simplicity, FIG. 6 shows fluid reservoir 84 located within the scrotum 86 of a male human being. Alternative anatomical locations for fluid reservoir 84 may exist. When distensible cylinders 82 are to be inflated such that penis 88 is placed in an erect condition, extensible section 56 is in a contracted state such that valve 10 acts as a check valve allowing flow only from fluid reservoir 84 to distensible cylinders 82. Valve 10 maintains penis 88 in an erect condition by preventing reverse fluid flow from distensible cylinders 82 to fluid reservoir 84. Penis 88 may be placed in a nonerect condition by the application of forces in the direction of the arrows 72 and 74, thus extending extensible section 56. When extensible section 56 is extended as shown in FIG. 4, fluid is allowed to flow from distensible cylinders 82 back to fluid reservoir 84. Forces in the direction of arrows 72 and 74 may be generated by pulling downward on fluid reservoir 84 within scrotum 86 in the direction of the arrow 90. This has the effect of pulling fluid reservoir 84 and supply tubing 42 in the direction of arrow 74. Since demand tubing 28 is affixed to cylinder(s) 82, an opposing reaction force will be exerted on valve 10 in the direction of arrow 72. When erection of penis 88 is desired, the user must avoid placing forces on said scrotum 86 or on fluid reservoir 84 in the direction of arrow 90. This insures that when fluid reservoir 84 is squeezed, valve 10 will be in the condition shown in FIGS. 1 and 3 and act as a check valve to permit the one-way flow of pressurized fluid to cylinder(s) 82.

FIG. 7 of the drawing shows a prosthesis designed to aid in the treatment of urinary incontinence. The system includes a fluid reservoir 84, a medical prosthetic pull valve 10, and an inflatable cuff occlusion device 92. The use of an inflatable cuff in a pressurizing system as an occlusion means for the treatment of urinary and fecal incontinence is disclosed by Robert Buuck in U.S. Pat. No. 3,863,622. Said fluid reservoir 84 is connected to valve 10 by means of supply tubing 42. Occlusion means 92 is connected to valve 10 by means of demand tubing 28. Fluid reservoir 84, again in the form of a squeezable bulb, is shown as surgically implanted inside the scrotum 86 of a male human being. Occlusion cuff 92 is operatively mounted around the urethra 94, such that urine passage through said urethra 94 is prevented when fluid pressure is applied through demand tubing 28 to occlusion cuff 92. When urine flow through urethra 94 is to be prevented, fluid reservoir 84 must be compressed so as to force fluid through valve 10 into occlusion device 92. At this time, extensible section 56 must be in its contracted state as shown in FIGS. 1 and 3 such that valve 10 behaves as a check valve preventing reverse fluid flow from occlusion cuff 92 back to fluid reservoir 84. When urine flow through urethra 94 is to be permitted, valve 10 can be opened by extending extensible section 56 to allow reverse fluid flow from occlusion device 92 back to fluid reservoir 84. Opposing forces in the direction of the arrows 72 and 74 can be applied to extend extensible section 56. Such opposing forces may be generated by applying a pulling force on fluid reservoir 84 within scrotum 86 in the direction of the arrow 90 in the same manner as described above with respect to FIG. 6.

It is anticipated that various changes may be made in the shape, construction and operation of the prosthetic pull valve and application systems therefor as disclosed herein without departing from the spirit and scope of the invention as defined by the following claims.

What is claimed is:

1. An implantable medical prosthetic pull valve comprising:
    a valve member;
    a valve support having a support channel therethrough;
    a resilient member extending between said valve member and said valve support;
    a seating member having a seating surface and further having a channel therethrough;
    an outer member attached to said valve support and said seating member and having an extensible section positioned between said valve support and said seating member such that the space between said valve support and said seating member is encased by said extensible section; and
    wherein said resilient member is compressible and wherein said extensible section has a contracted state and an extended state, so that when said extensible section is in said contracted state then said valve operates as a check valve, and opens when said resilient member is caused to compress and so that when said extensible section is in said extended state then said valve is caused to open.

2. A pull valve according to claim 1 in which said resilient member comprises a helical spring and said valve member is equipped with a groove into which said helical spring may be wedged so as to attach said helical spring to said valve member.

3. A pull valve according to claim 1 in which said valve support is equipped with a ridge and a flap to aid in locating and securing said resilient member.

4. A pull valve according to claim 1 in which said extensible section of said outer member comprises a circumferential fold or bulge in said outer member.

5. A pull valve according to claim 1 in which said seating member is composed of a material softer than said valve member rendering said seating member capable of conformably deforming to the shape of said valve member.

6. A pull valve according to claim 5 in which said seating channel of said seating member is capable of cooperating with said seating surface to releaseably grip said valve member.

7. A method of manufacturing a medical prosthetic pull valve comprising the steps of:
    molding an outer member in the form of a hollow tubular sheath having an extensible section comprising a circumferential fold or bulge in said outer member;
    assembling a valve support, resilient member, valve member, and seating member within said outer member;

attaching said valve support and said seating member to said outer member so that the space between said valve support and said seating member is encased by said extensible section.

8. The method of manufacturing a pull valve according to claim 7 also including the step of molding or cutting a seating surface into said seating member such that said valve member may be gripped by said seating member.

9. An implantable medical prosthetic system comprising:
- a fluid reservoir for implantation in a human being;
- an inflatable prosthetic structure for implantation in a human being; and
- a pull valve which is extensible to an open position by the application of external pulling force thereon, said pull valve being operatively connected in fluid flow communication between said fluid reservoir and said inflatable structure such that fluid pumped from said fluid reservoir will be retained by said pull valve within said inflatable structure when said pull valve is in a contracted state, and such that fluid will be allowed to drain through from said inflatable structure, through said pull valve, and into said fluid reservoir when said pull valve is extended by the application of pulling forces thereto.

10. The system of claim 9 in which said fluid reservoir comprises a bulb which may be used to place said pull valve in an extended state when said bulb is implanted inside a body by the application of external force on said bulb which will transmit pulling forces to said valve along its longitudinal fluid flow axis.

11. The system of claim 9 in which said inflatable structure comprises a plurality of distensible cylinders.

12. The system of claim 9 in which said inflatable structure comprises an occlusion cuff.

13. An implantable medical prosthetic pull valve comprising:
- a valve member;
- a valve support;
- a resilient member extending between said valve member and said valve support;
- a seating member mounted to allow fluid flow past said valve member in only one direction by movement of said resilient member in response to fluid pressure when said extensible section is not extended, and said valve member being displaced from said seating member when said extensible section is extended by external pulling forces to allow fluid flow past said valve member in both directions;
- an outer member surrounding said valve support and said seating member, and having an extensible section located between said valve support and said seating member.

14. A pull valve according to claim 13 wherein said extensible section is stretchable in a direction generally parallel to the direction of fluid flow through said pull valve to separate said valve member and said seating surface.

* * * * *